United States Patent [19]

Lee et al.

[11] Patent Number: 5,032,525

[45] Date of Patent: Jul. 16, 1991

[54] QUALITATIVE PROCESS AUTOMATION FOR AUTOCLAVE CURE OF COMPOSITE PARTS

[75] Inventors: C. William Lee, Centerville, Ohio; John B. Park, Brownsville, Calif.; Steven R. LeClair, Beavercreek, Ohio; Frances L. Abrams, New Carlisle, Ohio; Patrick H. Garrett, Loveland, Ohio; Ronald A. Servais, Dayton, Ohio

[73] Assignee: United States of America as represented by the Secretary of the Air Force, Washington, D.C.

[21] Appl. No.: 175,826

[22] Filed: Mar. 31, 1988

[51] Int. Cl.$^5$ .............................................. B29C 35/02
[52] U.S. Cl. ...................................... 436/55; 264/40.3; 264/40.6; 364/162; 422/62; 425/143; 425/149
[58] Field of Search ........................... 422/62; 436/55; 264/40.1, 40.3, 40.6; 364/148, 162, 221, 221.9; 425/135, 143, 149

[56] References Cited

U.S. PATENT DOCUMENTS

| | | | |
|---|---|---|---|
| 4,399,100 | 8/1983 | Zsolnay et al. | 422/62 |
| 4,455,268 | 6/1984 | Hinrichs et al. | 264/23 |
| 4,496,697 | 1/1985 | Zsolnay et al. | 526/60 |
| 4,515,545 | 5/1985 | Hinrichs et al. | 425/143 |

OTHER PUBLICATIONS

Servais, et al., "Intelligent Processing of Composite Materials," Sample Journal, (Sep./Oct. 1986), pp. 14–18.

Lee, "Composite Cure Process Control by Expert Systems," Proc. First Conf. on Composite Materials of American Society for Composites, Dayton, OH, (Oct. 7–9, 1986), pp. 187–196.

Lee, "Expert System Controlled Curing of Composites," 37th Canadian Chemical Engineering Conference, Montreal, Canada, (May 18–22, 1987).

Garrett, et al., "Qualitative Process Automation vs. Quantitative Process Control," American Control Conference, Minneapolis, MN, (Jun. 11, 1987).

Raulefs, et al. "An Architecture for Heuristic Cointrol of Real-Time Processes," Artificial Intelligence Center, Central Engineering Laboratories, FMC Corp. Santa Clara, CA, 6 Pages.

Sheu, et al. "Designing Control Systems with Knowledge," (TA5-9:30), School of Electrical Engineering, Purdue University, W. Lafayette, IN., pp. 941–946.

Shidler, et al., "Advanced Composites In-Process Controls/Inspection," AFWAL-TR-82-4051, Materials Lab, Wright-Patterson AFB, OH, pp. title, doc., 88–103.

Kays, "Exploratory Development on Processing Science of Thick-Section Composites," AFWAL-TR-8-5-4090, Materials Lab, Wright-Patterson AFB, OH, pp. Title Doc.

Primary Examiner—Jill Johnston
Attorney, Agent, or Firm—Bernard E. Franz; Donald J. Singer

[57] ABSTRACT

An automated, close-loop system for controlling the autoclave cure of fiber reinforced composites uses multiple expert systems hosted on different microprocessors running concurrently to control the cure process. This qualitative process controller uses sensory feedback to determine matrix material state-of-cure and then makes control decisions and executes control commands to the autoclave to attain desired material properties. The sensory information is interpreted and translated into a qualitative cure-state description by a system known as a parser hosted on a 68000 processor. The cure state description is then analyzed by the expert system known as the thinke hosted on another 68000 processor. The control decisions are determined using symbolic logic programmed as a rule-based paradigm generated from a human expert on the cure process. Once made, these control decisions are then posted to a blackboard hosted on an 80286 processor for execution by the autoclave feedback controller.

3 Claims, 11 Drawing Sheets

System Configuration for Automated Autoclave Cure

Fig. 1  System Configuration for Automated Autoclave Cure

Schematic of Information Flow Between the Three Expert Systems and the Autoclave Process

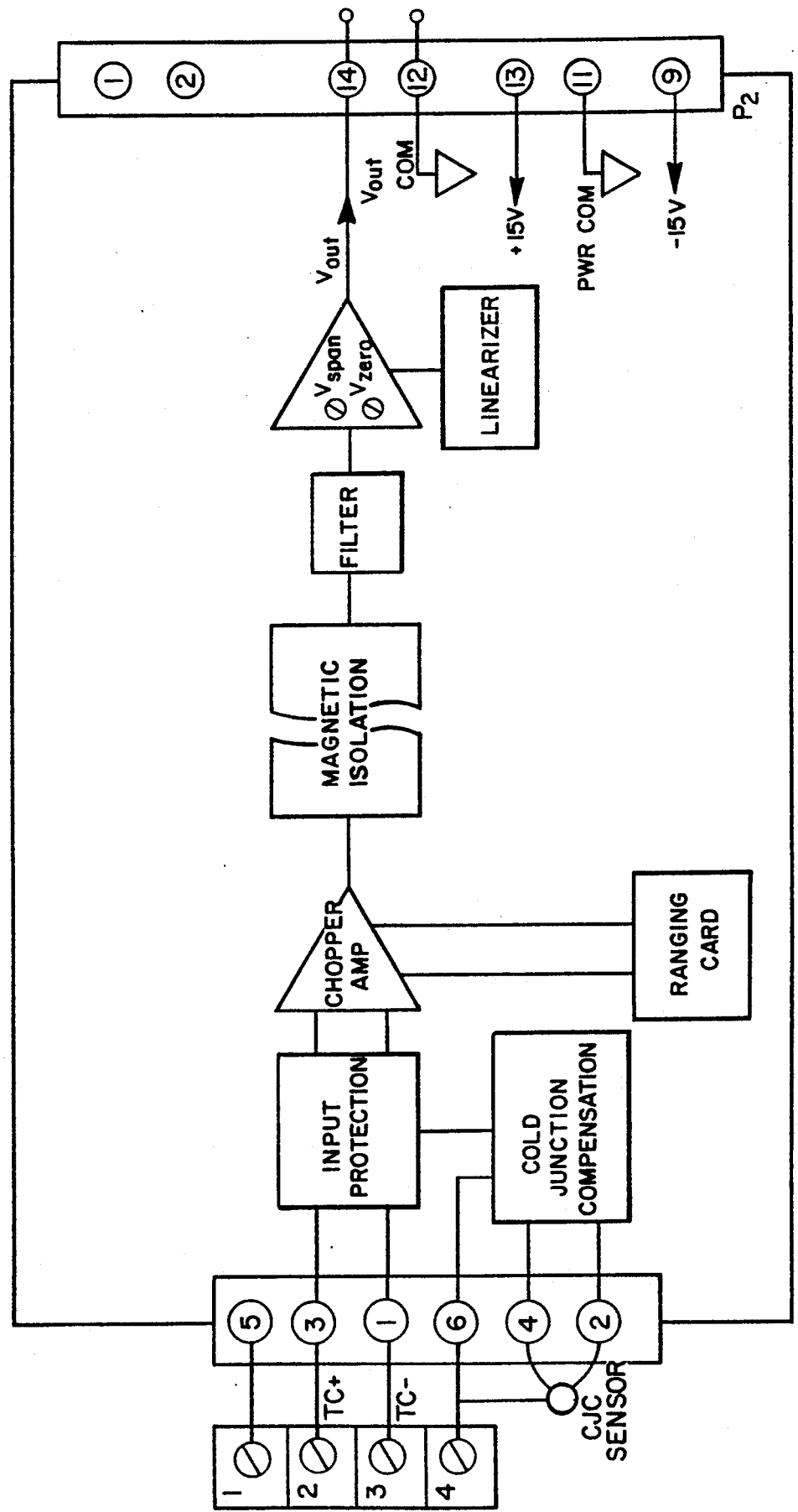
Fig. 3 FUNCTIONAL BLOCK DIAGRAM FOR THERMOCOUPLE SIGNAL CONDITIONING

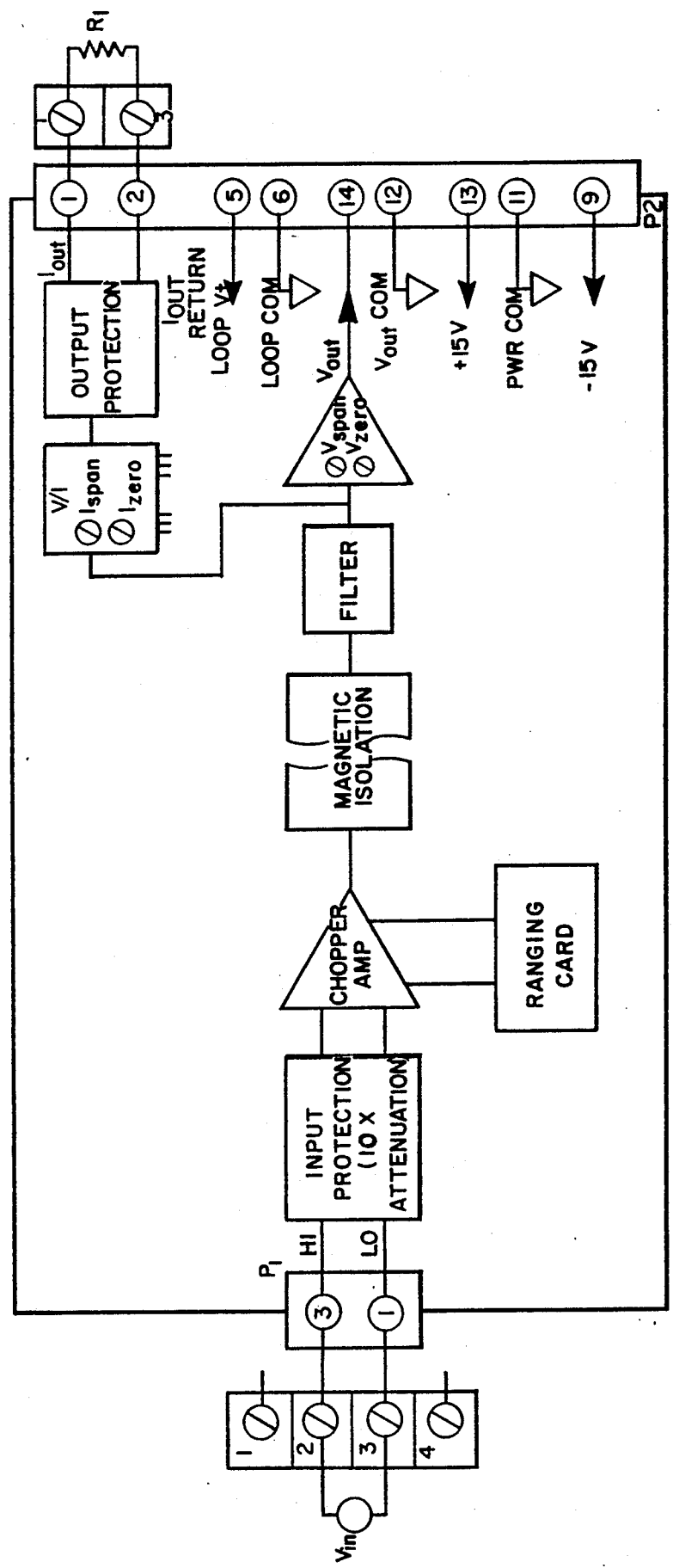
Fig. 4  Function Block Diagram for Pressure Sensor Signal Conditioning

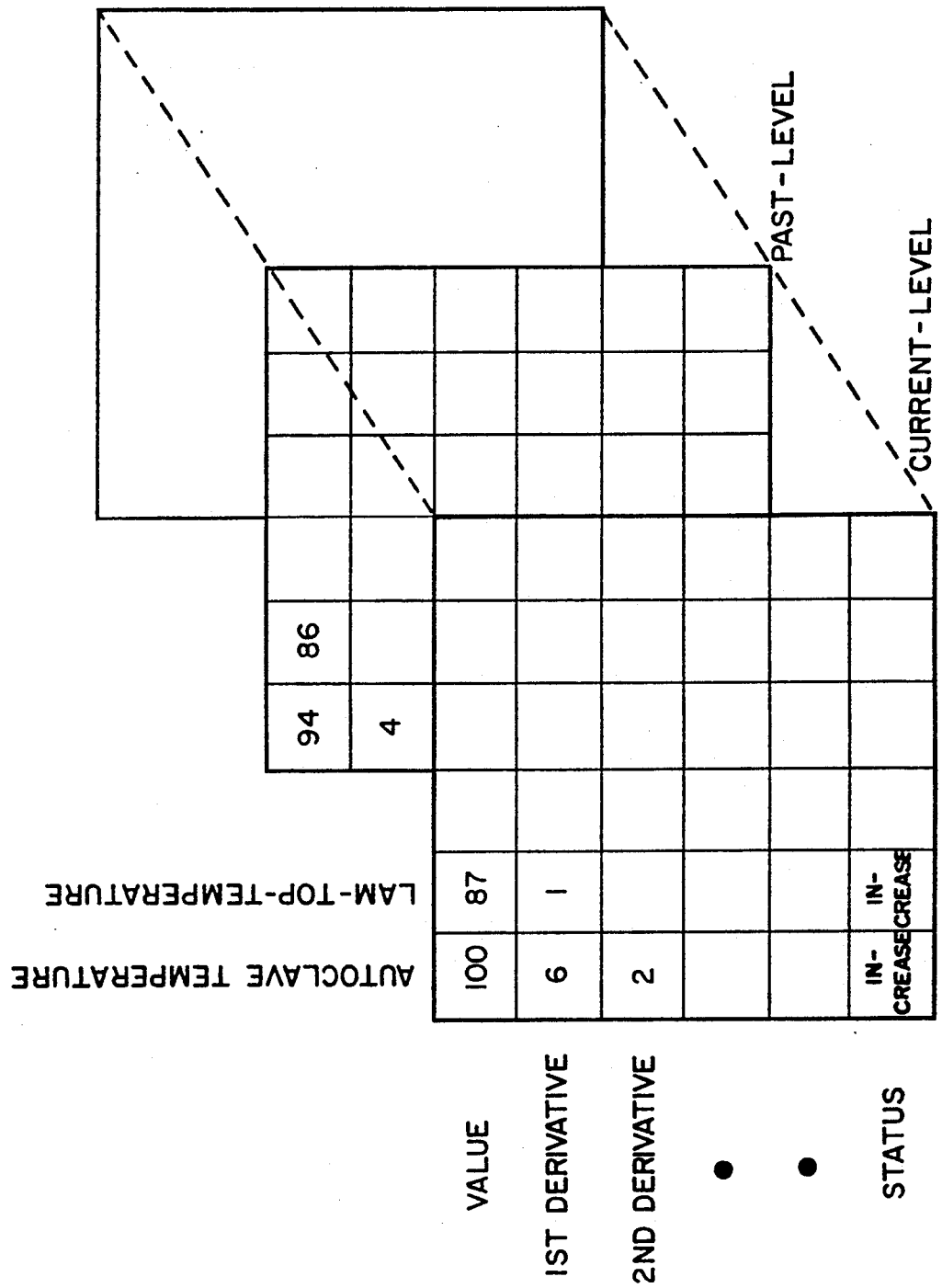
Fig. 5  EXAMPLE BLACKBOARD STRUCTURE

FRAME: COOLDOWN isa: process preconditions: current episode is CURE-EPISODE and
loss-factor is decreasing and
loss-factor is below a certain value and
part temperature has reached a certain value
OR
current episode is COOLDOWN-EPISODE effects: decrease autoclave-temperature

*Fig. 6* Sample Frame Structure Used in PARSER, THINKER and BLACKBOARD

QPA
COOLDOWN - EPISODE FRAME STRUCTURE

QUALITATIVE PROCESS AUTOMATION FOR AUTOCLAVE CURE OF COMPOSITE PARTS

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention relates to the general fields of manufacturing process control and artificial intelligence, and more particularly, to an automated system for developing a process cycle for composite parts and controlling that cycle based on the desired outcome of the process cycle in terms of processed materials properties.

2. Brief Description of the Prior Art

Composite materials consist of fibers imbedded in matrices which can be made of a variety of materials. The mixture of these components, if properly controlled and fabricated, offers improvements in properties which cannot be realized with most homogeneous materials because of the synergistic effect of the components of the mixture. The fibers offer strength and stiffness to organic matrix composites while the matrix provides a means of preventing buckling of the thin fibers by transferring load between them.

Another advantage of these materials is the tailorability of composite properties. The fibers can be oriented within a part to achieve strength in the most advantageous directions, decreasing the weight of materials needed for a specific requirement.

In order to realize the advantages of composites; however, extremely complex and controlled processing requirements must be met. Not only do the constituent materials have to be processed to each material's specific performance requirements, but the mixture then has to be fabricated from them which has precisely controlled ratios of fiber to matrix and the fibers must be oriented in such a manner as required to meet designed loads. In some processes, such as autoclave curing of thermosetting polymeric matrix composites, the development of matrix mechanical properties is achieved in the same process which determines fiber/matrix ratio and net part shape.

Most fabrication methods for composites involve the addition of heat or energy. One purpose of this heat is to initiate and sustain chemical reactions in thermosetting matrix polymers. Another purpose is to melt or reduce the resistance to flow of the matrix so that the composite can be formed into a shape and compacted into a final desired thickness. In some materials, a portion of the matrix present in the initial mixture may be pressed or bled out to achieve the final desired ratio of fiber to matrix. Whenever heat is applied, the danger exists that volatile components of the matrix, contaminants to the material, or products of chemical reactions may be vaporized and form bubbles within the matrix. Such bubbles, if not removed or suppressed, can result in porosity in the matrix which reduces mechanical properties.

Many composites are presently fabricated by the lamination of layers of premixed, or prepregged, fabric or unidirectional fibers impregnated with matrix, called prepreg. These layers are cut and stacked and then subjected to pressure and heat to form parts. In addition to the complexity represented by control of the fiber/matrix ratio, and prevention of porosity and the curing chemical reaction, the layers of the composite must all achieve relatively uniform properties in order to reduce localized deviations from the desired properties which might have a weakening effect on the entire part. Because of this, thermal and pressure gradients within a part and throughout a batch of parts must be controlled.

As an example of a typical process for fabrication of composites, the autoclave cure of polymeric matrix composites involves the stacking of layers of fabric or unidirectional fiber tows preimpregnated with controlled proportions of unreacted thermosetting polymer on a tool or mandrel. This stack is then placed in a sealed bag connected to a vacuum (and sometimes pressure) source and the bagged part is placed in an autoclave, which is a pressure vessel which can be heated. The autoclave temperature and pressure, and the bag vacuum and pressure are then manipulated with respect to a predetermined timing cycle. These cycles are generally established by modification of cycles which have been successfully used for similar parts and materials.

The above-mentioned means of developing process cycles have been improved somewhat by the incorporation of analytical models which serve to simulate the autoclave process. Such simulations can partially replace the more expensive trials on the autoclave when a full complement of data exists for a material and the processing vessel and tooling and bagging materials. This can reduce the number of trial parts considerably.

Typical current process cycles treat the various requirements of the composite process in sequence. Removal of volatile contaminants and entrapped air is first achieved by manipulation of vacuum combined with slightly increased temperatures, a process step known as debulking. The laminate is then compacted by manipulation of autoclave pressure and temperature to squeeze out excess matrix and press layers of prepreg together. This is done at a slightly elevated temperature which is sufficient to allow flow of the matrix but not high enough to initiate rapid curing. Finally, the temperature is raised to initiate rapid reaction and crosslinking of the polymeric matrix. Pressure may be applied within the bag at this point to suppress volatilization of contaminants or reaction products, generally water.

Such empirical reiterative approaches to cure cycle development are costly and time consuming and may not lead to true optimization, especially if, as has been the case, the process goals are treated in the sequential fashion outlined above. Specifically, autoclave trials require multiple manufacturing runs and extensive testing and qualification of new composite components. This cost can be reduced by use of analytical models to reduce the number of reiterations in the autoclave but these models require expensive generation of data on mechanical, thermal, viscous and diffusive properties of all materials used in the composite, bagging and tooling as well as autoclave characteristics. Even within the same materials, some of these properties may vary significantly, depending on quality assurance and handling history. Control of the above-mentioned autoclave cure is currently based on following within predetermined allowables, the predetermined cycles of temperature, pressure, and vacuum described above. The most advanced controllers are feed-back controllers which manipulate the autoclave temperature to maintain part temperatures, rates of heating and thermal gradients within predetermined constraints. Advanced controllers of this type may use matrix properties such as dielectric constants or ultrasonically measured modulus to determine flowability and compressability so that pressure can be controlled to take advantage of those properties in achieving the desired fiber/matrix ratio and suppressing bubble formation.

These cascade control systems are based on algorithms which correlate a limited number of predetermined factors. In the event of process events which fall outside controller limitations or fail to meet predetermined specification alarm conditions are triggered, and operator intervention is required to adjust or abort the cycle in progress.

U.S. patents of interest include a method U.S. Pat. No. 4,555,268 and a related system U.S. Pat. No. 4,515,545 to Hinrichs et al for controlling a curing process by measuring several parameters, comparing the values with predetermined values, and using the result of the comparisons to control the application of temperature and pressure in an autoclave. A system U.S. Pat. No. 4,399,100 and a related method U.S. Pat. No. 4,496,697 to Zsolnay et al describe a closed-loop automatic process control technique in which capacitance is measured to determine when to apply pressure.

In view of the complexity of the autoclave cure process and the interaction of multiple variables which are beyond direct control of the controller, two needs have been established in the industry. First, there has been a need for an improved means of optimizing cure cycles based on the extensive knowledge that has been developed in the process of developing and using analytical models to simulate the process. This would decrease the cost and learning and qualification time associated with the introduction of new, improved materials as well as the development costs of extending composites to new applications. It would also result in true optimization of the cure cycles which translates into reduced time and energy for processing.

Second, there has been a need to further automate the process of manufacturing composites by introduction of a more flexible controller which is capable of recognizing and intelligently responding to a greater variety of process behavior during the process. This capability offers improved reliability without tightening of precursor material specifications. Such tightened material specifications are costly because of the degree of process and handling controls required an the verification tests necessary to assure quality.

In summary, the need has been noted in the industry to increase automation of the processing of advanced composites by automating the development of cure schedules and improving the flexibility of response of in-process controllers.

SUMMARY OF THE INVENTION

An objective of the invention is to repeatedly produce high quality composite parts at a reduced processing cost.

This is accomplished according to the invention by monitoring autoclave and part sensors, determining from the sensor readings the state of the process, and then issuing control commands based on a set of heuristic rules. This use of sensor feedback in the control loop enables a customized cure for each part, without prior knowledge of material variance or part geometry effects.

The invention relates to an automated system and method for developing a process cycle for composite parts (with thermosetting polymeric matrix) and controlling that cycle simultaneously by means of symbolic logic based on the desired outcome of the processed material properties from the process and the influence of controllable process parameters on that outcome. During the process, the past and present state is constantly evaluated with respect to process goals and the controllable process parameters adjusted to cause the material to meet those goals.

An important feature is control process decision making based on the qualitative state of the polymeric material and the desired product goals in terms of multiple, selected properties.

The process determines the qualitative state of the polymeric material and stage of cure process through fusion of measured information from multiple, heterogeneous characteristics.

Selected characteristics including temperature (with thermocouples), Pressure and dielectric properties of the polymeric material matrix are measured at regular intervals.

Qualitative heat flow information is derived from an interpretation of the comparison of the thermocouple measurements with respect to each other and time.

Heat flow information is combined with dielectric property measurements to determine the state of reaction and flow properties of the polymeric material matrix.

Heat flow and state of reaction is represented symbolically and symbolic logic is used to compare these states with desired micromechanical properties of the composites.

A qualitative state of progress towards process goals is developed through symbolic comparison of desired and undesired process states.

Control decisions are made to manipulate pressure, temperature and vacuum controls based on the state of progress after each measurement cycle.

PUBLICATIONS AND UNPUBLISHED REPORT

The following papers and unpublished report relate to the invention.

1. LeClair, S. R., "Sensor Fusion: The Application of Artificial Intelligence to Process Control", 1986 Rochester FORTH Conference Proceedings, Rochester, N.Y., June, 1986, pp 15-22.

2. Park, J., "Toward the Development of a Real-Time Expert System", 1986 Rochester FORTH Conference Proceedings, Rochester, N.Y., June, 1986, pp 23-33.

3. Lee, C. W., "Composite Cure Process Control by Expert Systems", Proceedings of the First Conference on Composite Materials of American Society for Composites, Dayton, Ohio, Oct. 7-9, 1986, pp 187-196.

4. Garrett, P., Lee, C. W., & LeClair, S. R., "Qualitative Process Automation vs. Quantitative Process Control", American Control Conference Proceedings, Minneapolis, Minn., June, 1987.

5. Abrams, F. L. & Lee, C. W., "Expert System Curing of Epoxy/Graphite Composites", AIChE Conference on Emerging Materials, Minneapolis, Minn., August 1987.

6. Abrams, F. L., "Knowledge Base for Expert System Process Control/Optimization", ASM Polymer Composite Materials and Processing Conference Proceedings, Cincinnati, Ohio, Oct. 13-15, 1987.

7. Lee, C. W., "Expert System Controlled Curing of Composites", 37th Canadian Chemical Engineering Conference Proceedings, Montreal, Canada, May 18-22, 1987, pp 240-241.

The above seven papers are hereby incorporated by reference.

8. Abrams, F. L. & Lee, C. W., "An Expert System for Autoclave Cure", scheduled for the Fourth Annual International Polymer Processing Society Meeting, Orlando, Fla., May 8-11, 1988.

9. LeClair, S. R., Abrams, F. L., Lagnese, T. J., Lee, C. W.. Park, J. B., *Qualitative Process Automation for Autoclave Curing of Composite Parts: AFWAL-TR-87-4083*, AFWAL/MLTC, Wright-Patterson AFB, Ohio, Dec. 1987. (This is an unpublished technical report. A copy is attached to this patent application as filed, and is hereby incorporated by reference.)

BRIEF DESCRIPTION OF THE DRAWING

FIG. 3 is a functional block diagram for thermocouple signal conditioning:

FIG. 4 is a functional block diagram for pressure sensor signal conditioning;

FIG. 5 is a symbolic diagram of an example blackboard structure;

FIG. 6 is a chart showing a sample frame structure used in parser, thinker and blackboard.

DETAILED DESCRIPTION

Introduction

An automated closed loop system which plans and executes the autoclave cure process is disclosed. It has been discovered that a symbolic description of the active control parameters can be used to ascertain the current stare of the autoclave cure process and with heuristics rules plan and execute the future cure state directions. This automated system utilizes expert systems and other artificial intelligence based approaches to plan for future cure states. The unique feature offered by an expert system approach is its non-algorithmic approach to the computer program structure. The expert system can be programmed to be data- or event-driven, making this tool ideal for process control applications. Most previous approaches to control of batch processing involved a pre-programmed process cycle with feedback control such as a PID controller. The problem with this approach to process control is the inability of the program to adapt to unpredicted process events. The essence of process control is decision making in response to process events. Better decisions can be made if in-situ prediction of future outcomes is possible.

System Overview

The automated closed loop system (see FIG. 1) consists of specialized hardware and software which adaptively creates a custom cure for the specific composite matrix material part in an autoclave 120. The automated qualitative process system is closed loop and operates interactively with the autoclave and the subject part. This automated process system takes temperature and viscosity data as the active part control parameters. This sensory information, coupled with temporal reasoning, is used to determine the state of cure (the parser). The past and current cure state information is further processed (the thinker) to determine the future cure state and at this point temperature and pressure control commands are issued in a manner to reach the goal state.

Figure 1:
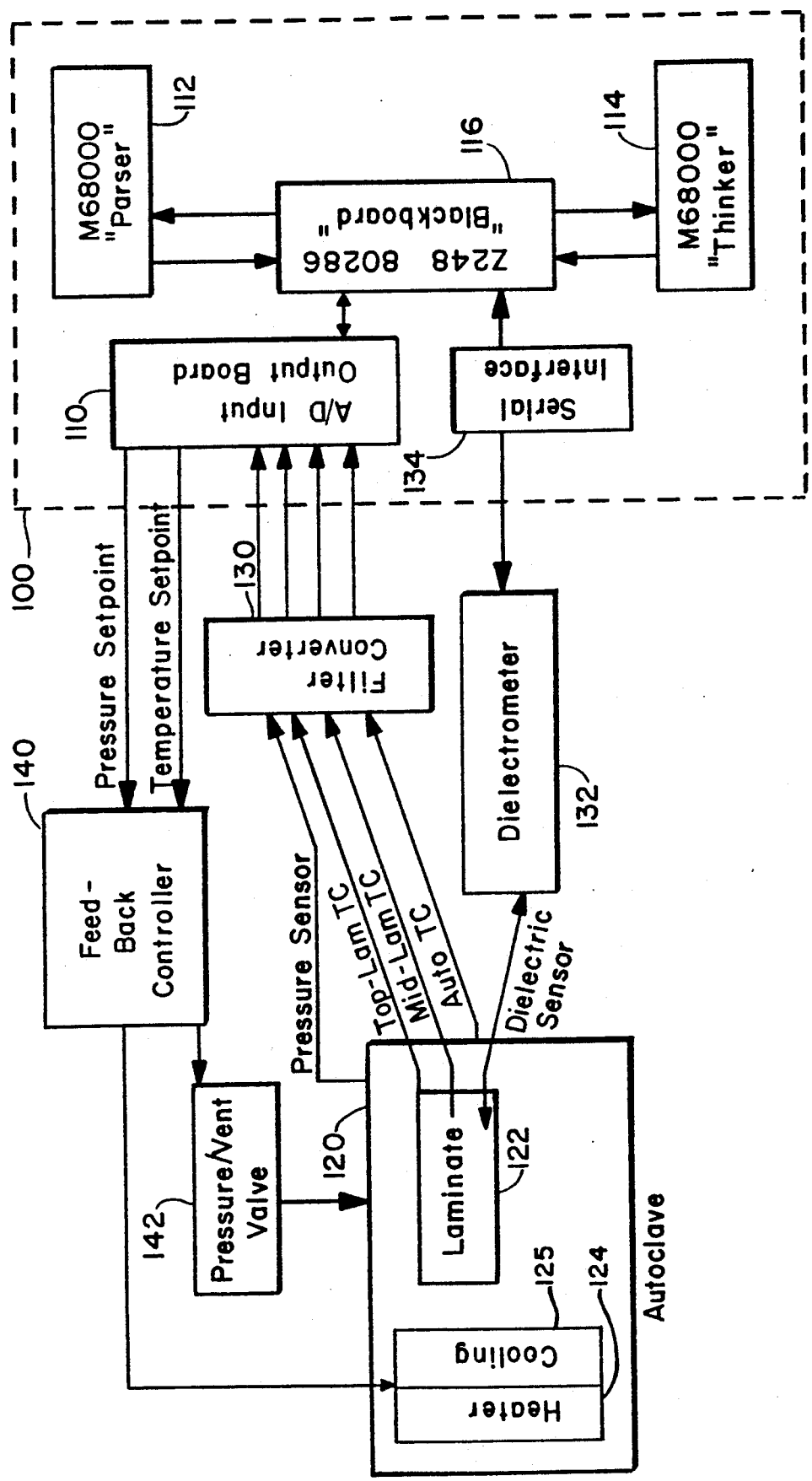
FIG. 1 is a block diagram of a system configuration for automated autoclave cure.

A system kernel 100 is comprised of three expert systems; a parser 112, a thinker 114, and a blackboard monitor 116, each hosted on separate processors. Two of the processors are Motorola 68000 based CPUs on the same bus; one to complete the parsing of the digital data for cure state determination (the Parser 112), and the other to determine the appropriate control actions given the current cure state (the Thinker 114). The third system, the backboard monitor 116, runs on a 80286 CPU, and handles all the communication among the CPUs, autoclave controller and is directly interfaced to the autoclave and part sensors. The blackboard module 116 is a Zenith Model #ZFX-248-50 from Zenith Data Systems, St. Joseph, Mich. The system has been used on the IBM XT and AT and on the Zenith 158 model, and is adaptable to any PC compatible with minimal effort and changes. Any RGB color monitor (not shown) with EGA board can be used with the module 116. The M68000 co-processor boards 112 and 114 are Model Pro68 2028 from Hallock Systems Inc., Herkimer, N.Y. (FIG. 1 shows the system with two boards but it can now run with one board for the two co-processors (mounted internal to the computer 116).

To provide the data processing flexibility and utility required, the system 100 includes a data conversion interface unit 110 with an "on-board microprocessor (DT2805 by Data Translation, Inc., Marlborough, Mass.). The microprocessor of the interface unit 110 provides for the analog to digital conversion of the input sensor signals and the digital to analog conversion for the output autoclave commands.

To meet the signal isolation and band limiting requirements of an industrial implementation, a filter converter 130 is provided which comprises an Analog Devices 3B series signal conditioning system. For the thermocouple sensors, type 3B47 units are used as shown by a functional block diagram in FIG. 3 (Model 3B47 J-03 Isolated Linerized Thermocouple Input), and for pressure, a type 3B41 unit is used as shown in FIG. 4 (Model 3B47-01 Isolated Wide Band V Input). The temperature sensors comprise a top-laminate thermocouple, a mid-laminate thermocouple, and an autoclave thermocouple, each of which is coupled to a FIG. 3 type device. A pressure sensor line is also shown in FIG. 1 coupled between the autoclave 100 and the filter converter 130. A power supply (not shown) type AC1301 is used with the filter converter 130. The units are from Analog Devices. Norwood, Mass.

A dielectric sensor from the laminate is coupled via a dielectrometer 132 (type Eumetrics II from Micromet Instruments, Inc. Cambridge, Mass.) and a serial interface unit 134 to a serial RS232 port of the processor 116. A feedback controller 140 (Micristar Programmable Controller with remote setpoint option from Research Incorporated Minneapolis, Minn.) has inputs from the interface board 110, and output to the heater and cooling units 124 and 125 in the autoclave. There is an output via a pressure/vent valve control unit 142 to the autoclave.

Figure 2:
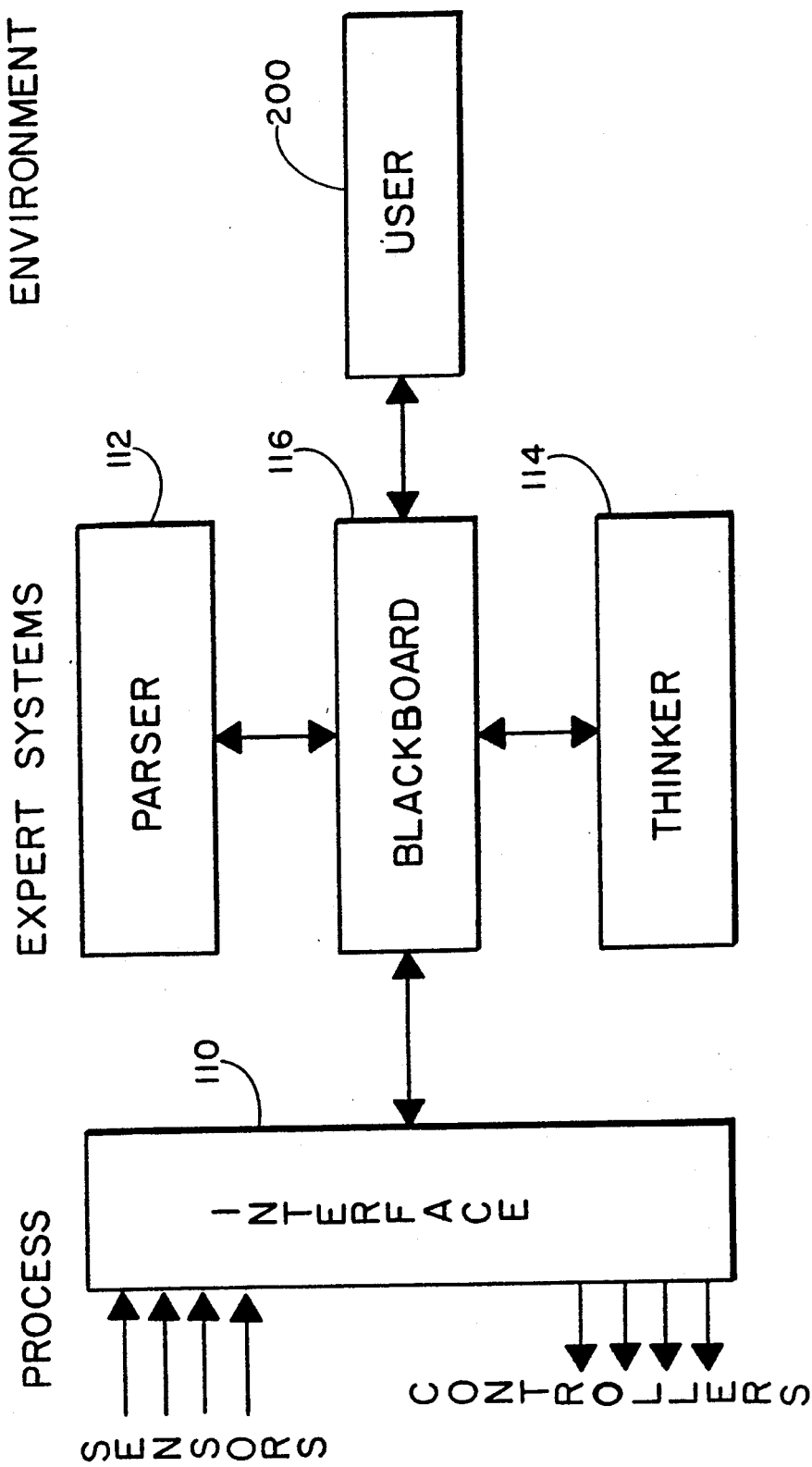
FIG. 2 is a symbolic block diagram of information flow between the three expert systems and the autoclave process.
Figure 7:
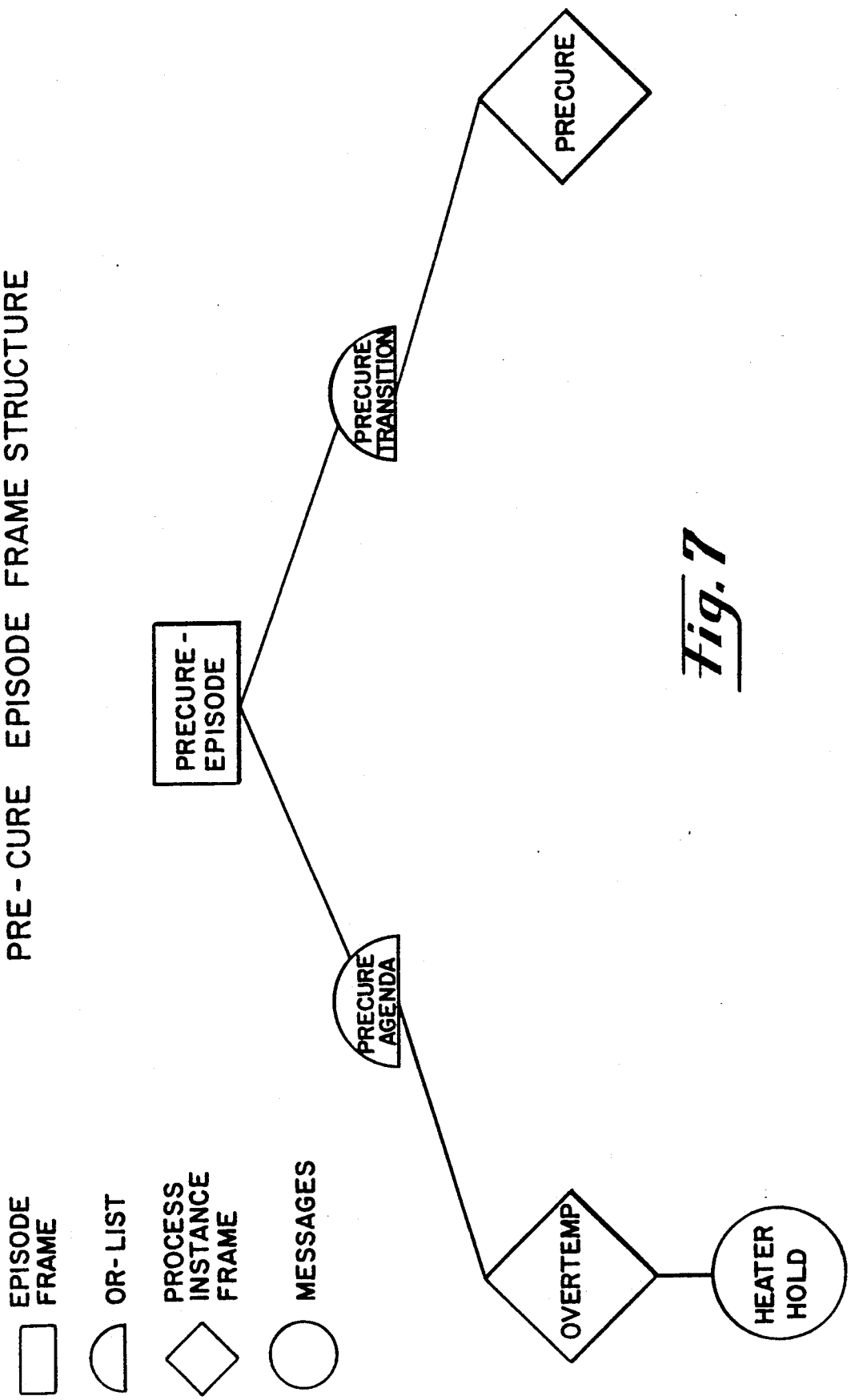
FIGS. 7, 8 and 9 are flow diagrams of the QPA frame structure for episode 1, episode 2, and episode 3, respectively.
Figure 8:
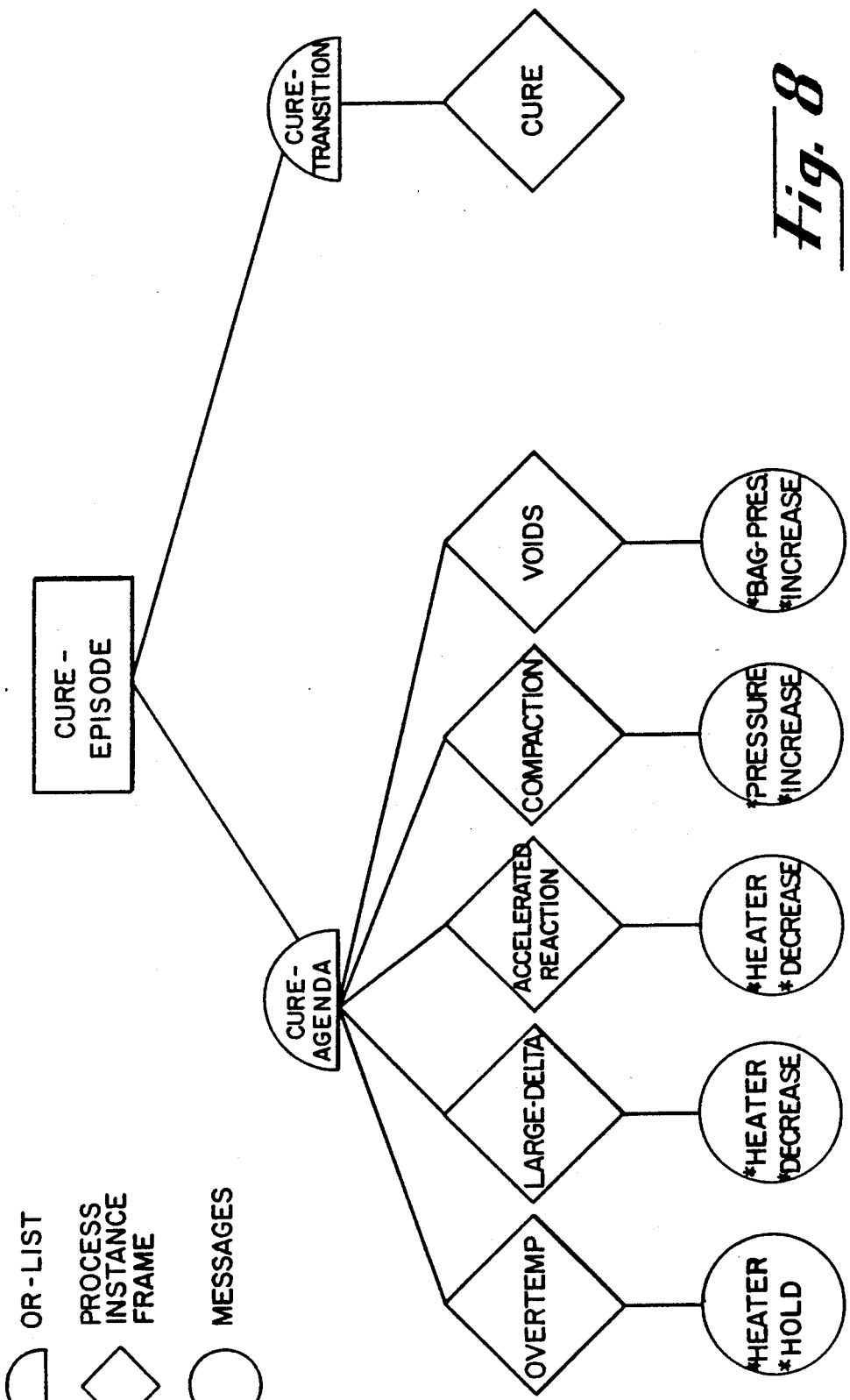
Figure 9:
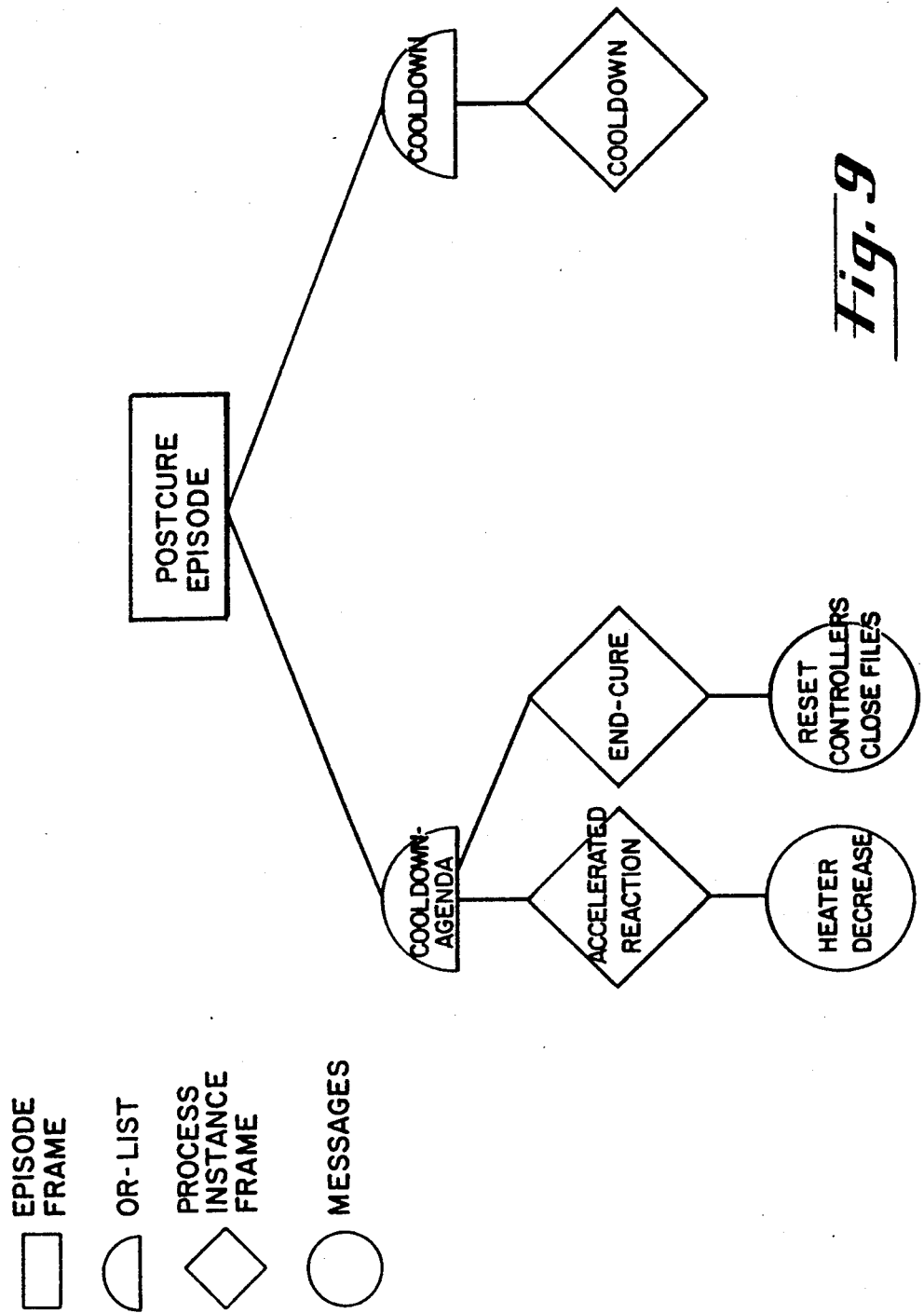
Figure 10:
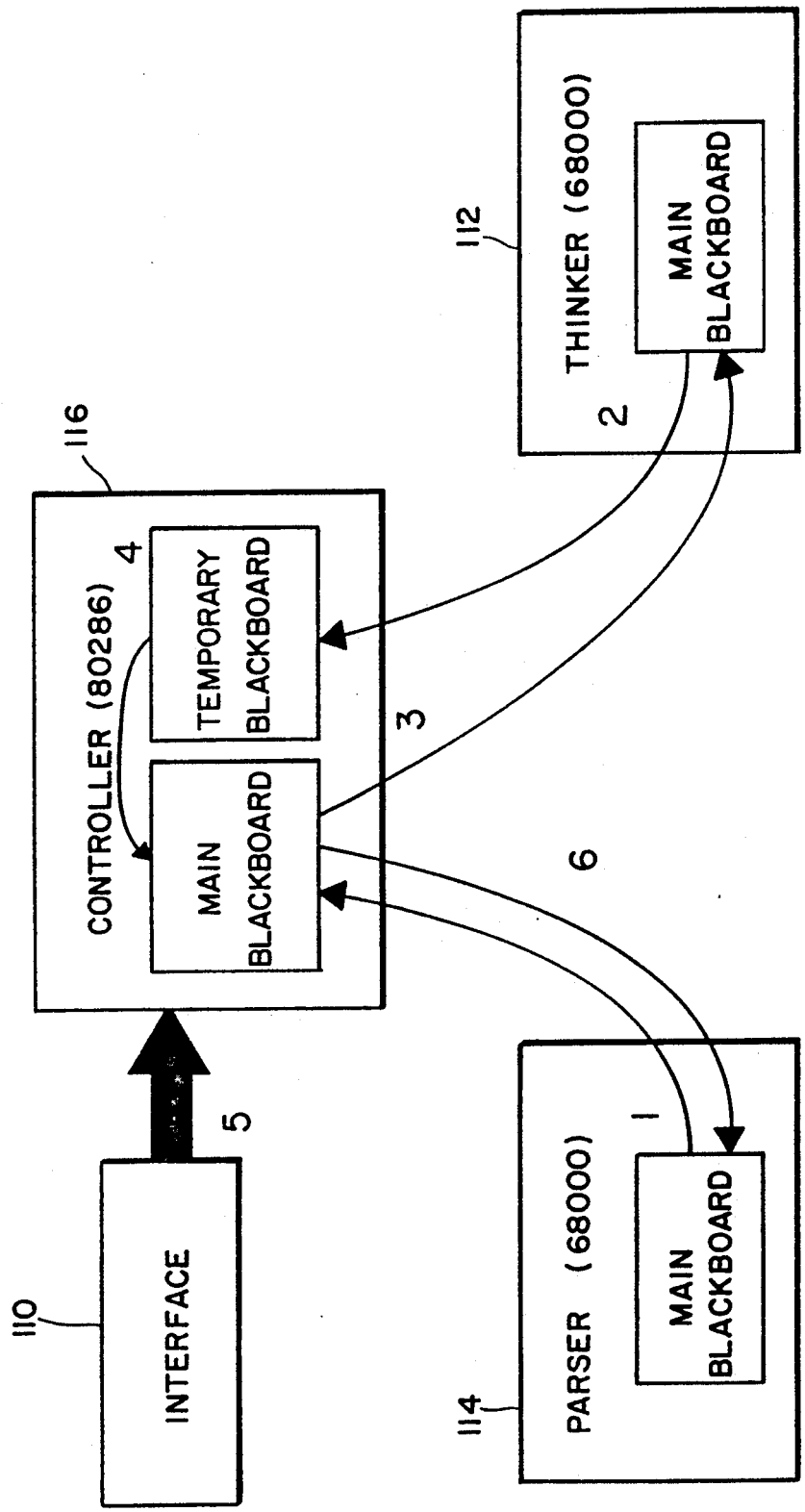
FIGS. 10 and 11 are interface flow diagrams for a multi-processor system and a dual-processor system, respectively.
Figure 11:
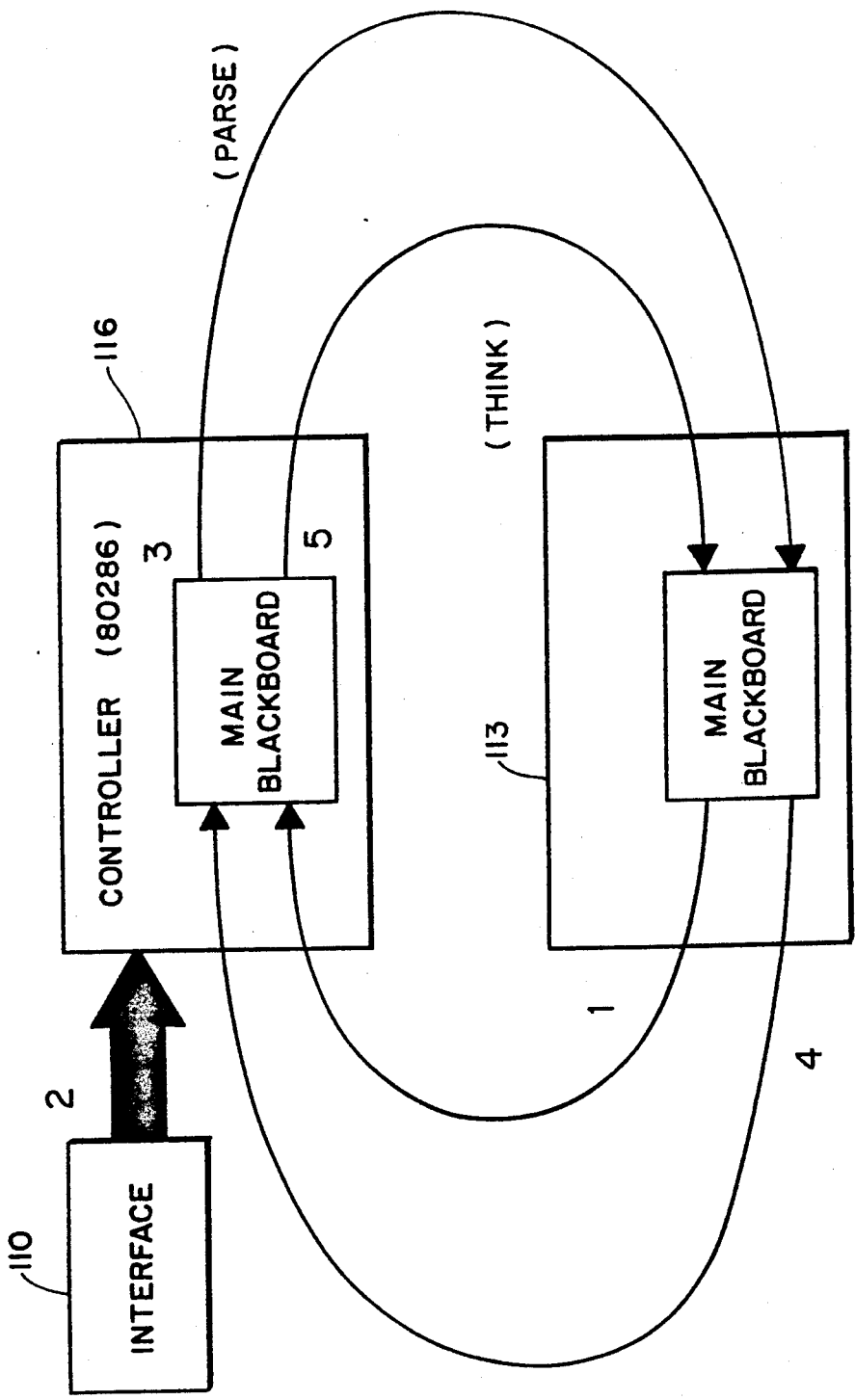

The autoclave 120 was supplied by Thermal Equipment Corp., Torrance, Calif., with the following specifications:
Maximum Working Temperature: 750° F.
Maximum Working Pressure: 200 PSIG
Working Area: 2'×2'
Pressurizing Medium: Nitrogen
Heat Source: Electrical
Maximum Controlled Heating Rate: 20° F./Min
Maximum Controlled Pressurization Rate: 10 PSIG/Min The flow of information from the autoclave to the computer and back to the autoclave is represented in FIG. 2. The sensor temperature and pressure information first passes through the Data Translation board 110 where the analog signal is converted to digital data. The digital data is posted to the Blackboard Monitor 116 where it is retrieved by the Parser Expert system 112. This sensor information is combined with past cure state information and interpreted into cure state information by the Parser, which is then passed back to the Blackboard Monitor. The Thinker Expert system 114 retrieves the current cure state information and, with a user defined knowledge base, determines the future cure state. The Thinker expert system then issues control commands, based upon the currently established cure state, which are posted to the Blackboard Monitor. These new control commands are further issued to the autoclave controller as new set points to be established within the autoclave.

Adaptive Interface to Sensor Fusion System

The adaptive interface for realtime data acquisition and control was designed on the basis of quantitative error analysis. The errors that occur in a sampled data system implementation include both device and system contributions, and effectively render a specific implementation nontransparent by the value of the total error accrued. A preliminary analysis of these errors is provided in the tabulation in Table 1 that describes a total sensor data uncertainty error of 0.59% of full scale (3° C.) input to the computer data bus in binary digital format. This realization approximates the goal of achieving equal device and system errors such that their total root-mean-square combination is a minimum. The value of decision operations provided to the process over the two d/a output channels are also constrained by this 3° C. uncertainty.

The design of the data acquisition and conversion system was driven by the need to interface a variety of sensors to a microcomputer and to allow for real-time data processing without compromise of data accuracy. To provide the data processing flexibility and utility required, a data conversion system with an onboard microprocessor was sought. The Data Translation 2801 series conversion products was determined suitable for near-term applications. A further enhancement to the data translation interface was to incorporate a more functional signal conditioning utility. To meet the signal isolation and band limiting requirements of an industrial implementation, the Analog Devices 3B series signal conditioning system was selected. To achieve the signal accuracy of interest, both thermocouple cold-junction compensation and linearization is mechanized in analog circuitry on a per-channel basis.

As mentioned previously, the 3B series Signal Conditioning I/O subsystem provides an interface to interconnect analog sensory signals to a data acquisition system. One of the input modules used in this system (3B47) are for J type thermocouple inputs providing cold junction compensation, amplification, and a 3-pole Bessel lowpass filter (0 to 3 hertz bandwidth). The inputs are attached to the backplane via screw terminals, and the module outputs are passed to the 26 pin ribbon connector on the left side of the backplane. A functional block diagram of the interconnect system is shown in FIG. 3. For monitoring the pressure signal, a 3B41 input module was used with inputs from ±10 mv to ±10V, with a 10 kHz bandwidth. The functional block diagram of the 3B41 module is shown in FIG. 4.

The DT2805 microprocessor of interface unit 110 was specifically configured for strict application requirements of the autoclave cure process. The DT2805 provides for the analog to digital conversion of the input autoclave control commands. The specific configuration for the current autoclave cure system allows for 16 channel analog to digital conversion, the storage of digital data via Direct Memory Access (DMA) to specific locations, conversion of analog data to digital for analog control and interrupt driven data retrieval. The DT2805 has been jumper selected for 16 single ended operation. The DT2805 offers selectible input gains and has been programmed for unity gain for temperature channels and 10× for the pressure channel.

Artificial Intelligent Approach to Automated Composite Cure

One of the major limitations in automating the cure process is that large amounts of software are generated to control the process. Additionally, the computational times of these algorithms are such that responses are not timely to control the process. This in itself is a not the total problem, a major problem is that the software is brittle when confronted with problems not foreseen by its developers. This is often the case when confronted with material variability, variations in lay-up, and complex geometry parts where the cure cycle is a difficult process to define in-situ.

The automated curing system was designed with the ability to utilize very generalized knowledge about the process and the process environment. This approach is a very common sense way to address composite cure. By utilizing simplified constraints of the cure process environment and rules which guide the cure process, a robust method of control is achieved.

The Construction of the Expert Systems

Program listings in FORTH are attached hereto as an Appendix

As mentioned previously, there are three expert systems that embody the total knowledge required to generate a cure plan, execute the plan and then control the cure environment. These expert systems are written in the FORTH language knowledge engineering shell called EXPERT 5. The software which supports these expert systems is distributed to 6 areas: Blackboard Definitions, Sensor Fusion, Blackboard Data Communication, Knowledge Base, Program Control and Autoclave Support Package. Each of these packages are tailored for the specific characteristics of the autoclave composite cure and are added to the EXPERT 5 environment. Although the Expert 5 system was used, the program listings could be readily modified to make use of other FORTH compilers and loaders.

The software programs are listed below and discussed in the order in which they would be loaded for running the autoclave, not necessarily the most logical grouping. The unit of programming in FORTH is the word, which is similar to a subroutine. Words which are defined in one program can be used by other programs in the system as long as they are loaded prior to being called by another word. Words can be executed at compile time or at runtime (after all words have been compiled).

Comments are delimited in FORTH by a backslash mark separated by a space and followed by the comment.

SHELL.COM

Expert system shell consisting of a Forth compiler/interpreter and, and Expert-5 (copyrighted by and available in compiled form from Thinkalong Software, P.O. Box 359, Brownsville, Calif. 95919).

SF68.BIN

Forth compiler and Expert-5 for the 68000 boards 112 and 114 for Parser and Thinker (also available with SHELL.COM from Thinkalong Software).

SHELL.COM and SF68.BIN are binary load images. SHELL.COM contains Intel 8088 machine instructions loadable under DOS while SF∈BIN contains Motorolla 68000 instructions loaded through the use of command in SHELL.COM.

The programming for the expert control system is developed under Expert-5 and the Forth environment. The program is divided into parts by function: BBDEF.SRS, SF3.SRC, BBSUP.SRC, KB.SRC,CNTL.SRC, and AUT.SRC (in the form of DOS ASCII files). The first 5 files define a control system with virtual sensor and control devices used in this implementation. Other supporting code may be included for chores such as data recording. The following is brief description of these files.

BBDEF.SRC

Blackboard definitions. This part of the code defines the symbols that are used by the Blackboard Monitor, the Parser, and the Thinker. Also included in this file are words for initialization and updating of the blackboard.

The blackboard defines a method for the different processors to communicate to each other. The current implementation uses a three dimensional array (indexed by LEVEL, CELL, and ENTRY) to store numerical and symbolic data (FIG. 5). Two LEVELs are defined; one for past states and one for current states. A partial list of CELLs is given in Table 2. For each CELL are defined the ENTRYs. The memory location (referenced by LEVEL, CELL, and ENTRY) can hold either a numerical or symbolic datum. In the case of a symbolic datum, it is represented by a TOKEN (which is just a number to the computer) defined by the user. A partial list of TOKENs is given in Table 3. Expert-5 facilitates the conversion of multi-dimensional data structure to linear memory addresses and tokenization of user defined symbols. BBDEF.SRC contains user's definition of the data structure and tokens used by the expert systems.

SF3.SRC

Sensor Fusion Shell. This part of the code defines the programming structure for the knowledge base. It provides support for constructing various lists and list processing methods.

The process knowledge is represented by process instances which are described by rules. The process is divided into episodes. In each episode, an agenda of process instances is described. The episodes agendas, and process instances are represented as lists. The qualitative reasoning knowledge is represented by lists of process variable influences and conflict resolution hierarchies. This Sensor Fusion Shell is built on Expert-5 for support on construction of these lists and methods of manipulating these lists. The structure of the knowledge base for a particular application is dictated by the definitions in this code.

BBSUP.SRC

Blackboard Monitor Support. This part of the code contains the virtual I/O and data processing support for the control system.

Parser acquires sensor data from the blackboard and Thinker posts control decision on the blackboard. Blackboard Monitor prepares the sensor data and posts the processed data on the blackboard for the Parser and implements the control decisions posted by the Thinker. The data processing may include filtering of sensor data generating temporal and/or spatial derivatives of sensor data, and conversion of certain data to symbolic form. The implementation of control decision may include interpretation of command message and determination of new setpoint for the process. The coding in BBSUP is not specific to any devices; it is written for "virtual"devices.

KB.SRC

Knowledge Base. This part of the code contains the representation of knowledge pertaining to autoclave curing of composites.

Specifically, there is knowledge used by the Parser for process state determination and knowledge used by the Thinker for control decision making. The Parser knowledge base is represented as FRAMEs. The process is divided into episodes and represented by process instances. An episode frame contains the agenda which is list of process instances to be considered when the process is in this episode. A process instance frame contains the preconditions for the process instance to be considered active, and the desired effects when it is active. The preconditions are specified by rules. A typical frame definition is given in FIG. 6.

The Thinker knowledge is declared in lists of controllable variables, their interactions, and conflict resolution hierarchy. Table d4 is an example of the INFLUENCES list.

CNTL.SRC

Program Control. This part of the code contains the procedures of program execution.

These are the FORTH words for controlling the execution of the program. It specifies, for example, such sequences as: get sensor data, process sensor data, post data, invoke Parser, invoke Thinker, actuate control element, update blackboard; and the repeated execution of this sequence.

DOSIO.SRC

DOS Input/Output Support. This part of the code contains the DOS interface software.

The expert system communicates to the user and peripherals through the PC-class computer under DOS (Disk Operating System). This part of the code is the interface between the expert system and the DOS environment. It supports file and serial port I/O.

AUT.SRC

Autoclave Support. This part of the code contains support for physical device I/O associated with the autoclave system.

There are two devices directly connected to the PC system input/output. One is the data acquisition board (DT2805) on the PC bus and the other is a dielectrometer (Micromet) connected to the PC's asynchronous communication port (serial port). The system controls the data acquisition board directly through PC I/O registers using binary control codes and the dielectrometer through DOS logical device COM1 or COM2 using ASCII control codes. This Part of the program contains the control of these devices and conversion of raw data (such as a 12-bit value from DT2805) to the form used by the expert systems (such as a temperature in degrees Fahrenheit). Also contained in this code is the association of actual devices to the virtual devices defined in BBSUP.

Curing Strategy

The approach to curing a graphite epoxy composite part was to have the part itself guide its own cure. Feedback from the part to the Automated Curing program was acted upon as if by an expert in composite processing. This is a very unique approach which avoids curing problems associated with material/part geometry variability which is inherent in all composites. The premise for this approach to adaptively curing composite parts was to try to accomplish the physical property goals for the material. These physical property goals are to be based upon the micromechanical requirements of the composite part design. Further, by taking a qualitative process control approach, the cure process relationships to these design properties are established. The process relationships were then used by the expert system to dynamically develop the cure process control in-situ, based on current and past information of the cure process state. No preconceived cure process cycle was utilized, which allowed for greater flexibility to adapt to part history, composite material variability and to part geometry complexity. In the design of composites, mechanical properties can be related to the micromechanical properties of the fibers and matrix as well as the interaction of these constituents. The physical properties of importance to the current level of micromechanical design which are also under the control of the curing process are: fiber volume of the laminate, uniformity of fiber and matrix distribution, porosity of the laminate, modulus of the matrix, and the residual stresses in the laminate.

In order to achieve control of these processes a number of subprocesses were established, with goals which are user determined, based on design considerations. Progress toward the goals is measured and/or calculated throughout the process and control actions determined by expert knowledge about the effects of the process on that progress. Specifically, the matrix modulus goal is set to be a minimum value at or above a given temperature. This value is arbitrarily determined or related to desired design properties although it must be within the limitations of the material. Progress toward the goal is measured by a combination of dielectric properties and sensed temperatures regulated by increase or decrease of the heat flow into the laminate. The rate of progress towards this goal is kept as high as possible to save time in the cure but is subject to limits which are based on the need to simultaneously achieve other goals and prevent damage to the part.

The fiber volume goal is set to be a range of values determined by design limits and is regulated by the application of autoclave pressure. This property is highly dependent upon part history and lay-up. Laminate response to pressure (flow) is also temperature dependent. The rate of progress towards this goal is also kept as high as possible to increase efficiency. The compaction goal is approached by increase in temperature just as the cure goal is initially. However, as the cure progresses, further application of heat conflicts with the goal of compaction. Compaction after gelation is likely to result in matrix damage.

The goal of uniformity in matrix fiber mixing is regulated by minimizing temperature gradients through the laminate during compaction and cure. This method is also used currently for minimizing residual stresses. Gradients are minimized by removal of heat from the hotter portions of the laminate. This action is in conflict with the action taken to achieve desired matrix modulus and compaction. Voids are regulated by removing volatiles via a vacuum, and by an increase of bag pressure when the vapor pressure of volatile components exceeds the hydrostatic pressure of the matrix. This goal can conflict with the goal of achieving compaction because increased bag pressure negates the compacting effect of the autoclave pressure.

The resolution of conflicts is also user-determined. For example, the rate of heat flow into the laminate may be slowed, decreasing the rate of cure, to allow for compaction to proceed to completion before gelation. In cases where design criteria can be loosened the conflicts can be reduced by allowing one goal to override the less critical ones. Other restraints such as the temperature and performance limitations of the autoclave and lay-up materials associated with the part are user defined and adjusted constants.

Determination of progress towards the goals is made by inference of the current and past process states from sensor information. The primary sensors are thermocouples which are located in an array in order to give spatial as well as temporal gradient information. Heat flow sensors also could serve this purpose. Information about the flow of heat is derived from spatial and temporal gradients of temperature. Values of temperature measurements are also necessary to relate to limits of the process vessel and the materials used in the process. Dielectric sensors are used to determine the progress towards the desired modulus and glass transition temperature of matrix and to determine the ability of the matrix to flow for purposes of compaction.

The system is not sensor specific. Any sensor which measures temperature or temperature gradients can be used in place of the thermocouples. Any sensor which can determine the modulus of the matrix or of the composite may be used for assessing degree of cure.

The parser 112 and the thinker 114 are described above as separate microprocessors, but they may be combined to use a single type M68000 microprocessor. The only software modification required is in the program control package.

It is understood that certain modifications to the invention as described may be made, as might occur to one with skill in the field of the invention, within the scope of the appended claims. Therefore, all embodiments contemplated hereunder which achieve the objects of the present invention have not been shown in complete detail. Other embodiments may be developed without departing from the scope of the appended claims.

TABLE 1

PRELIMINARY SENSOR FUSION SYSTEM SIGNAL CONDITIONING AND CONVERSION ERROR BUDGET

| Element | Error (% FS) | Comment |
| --- | --- | --- |
| Sensor | 0.10 | Linearized Type-J |
| Interface | 0.10 | Cold junction compensator |
| Amplifier | 0.33 | Av = 366, Vcm = 1 V |
| Filter | 0.10 | 3-pole Bessel, $f_c$ = 3 Hz |
| AMUX | 0.01 | 16-channel CMOS |
| Amplifier | 0.06 | Av = 1 scaling |
| S/H | 0.02 | ta = 10 ns |
| A/D | 0.05 | 12-bit successive approx. |
| Sinc | 0.05 | Average signal attenuation |
| Intersample | 0.19 | fs = 66 mHz |
| TOTAL ERROR DATA | 0.59% FS | 3° C. UNCERTAINITY |

TABLE 2

Identification of Cells in BLACKBOARD wm-cell GOAL
wm-cell CUR-EPISODE
wm-cell MESSAGE1 wm-cell MESSAGE2
wm-cell MESSAGE3 wm-cell MESSAGE4
wm-cell LAM-TOP-TEMP
wm-cell LAM-MID-TEMP
wm-cell AUTOCLAVE-TEMP
wm-cell VISCOSITY
wm-cell LOSS-FACTOR
wm-cell PRESSURE
wm-cell TIME-COUNT
wm-cell &PRECURE
wm-cell &CURE
wm-cell &POSTURE
wm-cell &ENDCURE
wm-cell &VOIDS
wm-cell &COMPACTION
wm-cell &OVERTEMP
wm-cell &large-delta
wm-cell &RXNTEMP
wm-cell &EXOTHERM

TABLE 3

Tokens --
Information Passed to the PARSER and THINKER
Through the BLACKBOARD

| | | |
| --- | --- | --- |
| T: *ON | T: *OFF | T: *HOLD |
| T: *COOLERON | T: *COOLEROFF | |
| T: *PRESSURE-ON | T: *PRESSURE-OFF | |
| T: *RISING | T: *STEADY | T: *FALLING |
| T: *PRECURE | T: *CURE | T: *POSTCURE |

TABLE 3-continued

Tokens --
Information Passed to the PARSER and THINKER
Through the BLACKBOARD

| | |
| --- | --- |
| T: *PARSE | T: *THINK |
| T: *SUCCESS | T: *FAIL |
| T: *INCREASE | T: *DECREASE |
| T: *EXOTHERM | T: *VOIDS |
| T: *PRE-E2 | T: *POST-E2 |
| T: *MIN-E2 | T: *MAX-E2 |
| T: *COMPACTION | T: *OVER-COMPACT |
| T: *DEGREE-OF-CURE | |
| T: *HEATER | |
| T: *PRESSURE | T: *BAG-PRESSURE |
| T: *TIMING | |
| T: *ACTIVE | |

TABLE 4

Qualitative Process Knowledge Base Used in THINKER Which is Used to Describe All Known Process Interactions. First Line Reads: The Heater Positively INFLUENCES the Autoclave Temperature.

| | |
| --- | --- |
| I+(*heater | autoclave-temp) |
| I+(autoclave-temp | lam-top-temp) |
| I+(lam-top-temp | lam-mid-temp) |
| I+(lam-mid-temp | *degree-of cure) |
| I+(lam-mid-temp | *exotherm) |
| I+(lam-mid-temp | *pre-e2) |
| I+(*degree-of cure | *post-e2) |
| I−(*pressure | *voids) |
| I+(*pressure | *compaction) |
| I−(*pre-e2 | *over-compact) |

What is claimed is:

1. A method of automated realtime cure cycle generation and control of a thermosetting polymeric material in an autoclave, suing a qualitative process control approach for adaptively curing composite parts to accomplish physical property goals for the material, these physical property goals being based upon micromechanical requirements of a composite part design, wherein cure process relationships to the design properties are established, said goals being based on mechanical properties related to the micromechanical properties of fibers and matrix of the material as well as the interaction of these constituents, physical properties under the control of the curing process being: fiber volume of the laminate, uniformity of fiber and matrix distribution, porosity of the laminate, modulus of the matrix, and residual stresses in the laminate, control of these processes being achieved by establishing control of a number of subprocesses, with subprocess goals which are user determined and which include subprocess goals related to the modulus of the matrix, fiber volume, uniformity in matrix fiber mixing, compaction, and regulation of voids; said method comprising the following steps (a) to (d) for each of the subprocess goals:

a. in-situ measuring of selected characteristics of the polymeric material in multiple, selected locations, including using temperature sensors located in an array in order to give spatial as well as temporal gradient information, and using dielectric sensors for measuring dielectric temporal gradients of the polymeric material matrix to determine progress towards desired modulus and glass transition temperature of matrix and to determine the ability of the matrix to flow for purposes of compaction;

b. determining progress toward the subprocess goals throughout the process and control actions determined by expert knowledge about the effects of the process on that progress, process relationships being used by the expert system to dynamically develop the cure process control in-situ, based on current and past information of the cure process state from sensor information, which includes determining the state of the polymeric material and stage of cure process by combining heat flow information with dielectric temporal gradient measurements form step (a) to determine the state of reaction and flow temporal gradients of the polymeric material matrix;

c. control process decision-making based on the state of the polymeric material and the desired product goals in terms of multiple, selected properties, which comprise said physical properties under the control of the curing process;

d. performing control actuation by manipulating autoclave temperature, pressure and vacuum;

wherein the subprocess goal related to the modulus of the matrix is set to be a predetermined minimum value at or above a given temperature, progress toward this subprocess goal being measured by a combination of dielectric temporal gradients and sensed temperatures regulated by increase or decrease of the heat flow into the laminate, the rate of progress towards this goal being kept as high as possible to save time in the cure but being subject to limits which are based on the need to simultaneously achieve other goals and prevent damage to the part;

wherein the subprocess goal related to the fiber volume is set to be a range of predetermined values regulated by the application of autoclave pressure, the rate of progress towards this goal being also kept as high as possible to increase efficiency;

wherein the subprocess goal related to compaction is initially approached by increase in temperature just as the cure goal is;

wherein the subprocess goal related to uniformity in matrix fiber mixing is regulated by minimizing temperature gradients through the laminate during compaction and cure, gradients being minimized by removal of heat from the hotter portions of the laminate;

wherein voids are regulated for the subprocess goal related to regulation of voids by removing volatiles via a vacuum, and by an increase of bag pressure when the vapor pressure of volatile components exceeds the hydrostatic pressure of the matrix.

2. A process control system for automated realtime cure cycle generation and control of a thermosetting polymeric material in an autoclave;

using a process control approach for adaptively curing composite parts to accomplish physical property goals for the material, these physical property goals being based upon micromechanical requirements of a composite part design, wherein cure process relationships to the design properties are established, said goals being based on mechanical properties related to the micromechanical properties of fibers and matrix of the material as well as the interaction of these constituents, physical properties under the control of the curing process being: fiber volume of the laminate, uniformity of the fiber and matrix distribution, porosity of the laminate, modulus of the matrix, and residual stresses in the laminate, control of these processes being achieved by establishing control of a number of subprocesses, with subprocess goals which are user determined;

wherein the process control system comprises:

a processor kernel comprising a blackboard module, a parser module coupled to the blackboard module, and a thinker module coupled to the blackboard module;

wherein the autoclave includes a plurality of sensors, including temperature sensors located in an array, dielectric sensors, viscoelastic property sensors, and a pressure sensor;

a feedback (PID) controller coupled to the autoclave for controlling heating, cooling and pressure in the autoclave;

interface means coupled between the sensors of the autoclave and the blackboard module, including filter converter means coupled to the temperature and pressure sensors and a dielectrometer unit coupled to the dielectric sensors, and outputs from the interface means coupled to the feedback (PID) controller;

wherein the blackboard module includes means for inputting data from said sensors via said interface means, for providing data relating to in-situ measurements of selected characteristics of the polymeric material in multiple, selected locations;

wherein the parser module includes means for reaching conclusions concerning system and material property status, including means for taking sensor data from the blackboard module and means for determining the state of the polymeric material and stage of cure process by combining heat flow information with dielectric temporal gradient measurements from the blackboard module to determine the state of reaction and flow properties of the polymeric material matrix and including using data from the temperature sensors located in an array in order to give spatial as well as temporal gradient information, and using data from the dielectric sensors for information relating to measurements of dielectric temporal gradients of the polymeric material matrix to determine progress towards desired modulus and glass transition temperature of matrix and to determine the ability of the matrix to flow for purposes of compaction; wherein the means for determining the state of the polymeric material and stage of cure process includes means for determining progress toward the subprocess goals throughout the process, process relationships being used by the expert system to dynamically develop the cure process control in-situ, based on current and past information of the cure process state from sensor information, and means for passing data relating to the conclusions of the system status from the parser module to the blackboard module;

wherein the thinker module comprises means for taking and using the data relating to the conclusions of the system status from the blackboard module for control process decision making relative to the state of the polymeric material and the desired product goals in terms of multiple, selected properties, using control actions determined by expert knowledge about the effects of the process on that progress, and means for passing the control decisions as control data to the blackboard module; and means for performing control actuation by passing the control data from the blackboard module via the interface unit and the feedback controller to manipulate autoclave temperature, pressure and vacuum;

wherein a matrix modulus subprocess goal is set by said control data from the thinker module to be a predetermined minimum value at or above a given temperature, progress toward the matrix modulus subprocess goal being measured by a combination of dielectric temporal gradients and sensed temperatures regulated by increase or decrease of the heat flow into the laminate, the rate of progress towards this goal being kept as high as possible to save time in the cure but being subject to limits which are based on the need to simultaneously achieve other goals and prevent damage to the part;

wherein a fiber volume subprocess goal is set by said control data from the thinker module to be a range of predetermined values regulated by the application of autoclave pressure, the rate of progress towards this goal being also kept as high as possible to increase efficiency;

wherein said control data from the thinker module causes a compaction subprocess goal to be initially approached by increase in temperature just as the cure goal is;

wherein a subprocess goal of uniformity in matrix fiber mixing is regulated by said control data from the thinker module by minimizing temperature spatial gradients through the laminate during compaction and cure, gradients being minimized by removal of heat from the hotter portions of the laminate;

wherein voids are regulated by said control data from the thinker module for a subprocess goal by removing volatiles via a vacuum, and by an increase of bag pressure when the vapor pressure of volatile components exceeds the hydrostatic pressure of the matrix.

3. The system according to claim 2, wherein the thinker module includes means for the resolution of conflicts, including generating control data for slowing the rate of heat flow into the laminate, thereby decreasing the rate of cure, to allow for compaction to proceed to completion before gelation.

* * * * *

UNITED STATES PATENT AND TRADEMARK OFFICE
CERTIFICATE OF CORRECTION

PATENT NO. : 5,032,525

DATED : July 16, 1991

INVENTOR(S) : C. William Lee, et al

It is certified that error appears in the above-identified patent and that said Letters Patent is hereby corrected as shown below:

On the title page, In the Abstract:

Line 13, "thinks" should read --thinker--.

Col. 2, line 64, a comma should follow "following".

Col. 4, line 21, "Pressure" should not be capitalized.

Col. 5, line 46, "stare" should read --state--.

Col. 6, line 61, changing the first period to read --,--.

Col. 6, line 66, should begin a new paragraph.

Col. 6, line 68, a comma should follow "Incorporated".

Col. 7, line 6, the second period should be a comma.

Col. 9, line 33, "SF∈BIN" should read --SF68.BIN--

Col. 13, line 35, "UNCERTAINITY" should read --UNCERTAINTY--.

Col. 14, line 36, "suing" should read --using--.

Signed and Sealed this

Sixth Day of April, 1993

Attest:

STEPHEN G. KUNIN

*Attesting Officer*    Acting Commissioner of Patents and Trademarks